(12) United States Patent
Abbate

(10) Patent No.: US 7,476,245 B2
(45) Date of Patent: Jan. 13, 2009

(54) POLYMERIC STENT PATTERNS

(75) Inventor: Anthony J. Abbate, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 138 days.

(21) Appl. No.: 11/205,858

(22) Filed: Aug. 16, 2005

(65) Prior Publication Data

US 2007/0043426 A1 Feb. 22, 2007

(51) Int. Cl.
  *A61F 2/06* (2006.01)
(52) U.S. Cl. ...................................... 623/1.15
(58) Field of Classification Search .................. 623/1.1, 623/1.12, 1.15, 1.16, 1.18, 1.2, 1.3
See application file for complete search history.

(56) References Cited

U.S. PATENT DOCUMENTS

| | | | |
|---|---|---|---|
| 3,687,135 A | 8/1972 | Stroganov et al. |
| 3,839,743 A | 10/1974 | Schwarcz |
| 3,900,632 A | 8/1975 | Robinson |
| 4,104,410 A | 8/1978 | Malecki |
| 4,110,497 A | 8/1978 | Hoel |
| 4,321,711 A | 3/1982 | Mano |
| 4,346,028 A | 8/1982 | Griffith |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallsten et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |

(Continued)

FOREIGN PATENT DOCUMENTS

DE 44 07 079 9/1994

(Continued)

OTHER PUBLICATIONS

Search Report for PCT/US2006/030954 filed Aug. 4, 2006, mailed Nov. 29, 2006, 11 pgs.

(Continued)

*Primary Examiner*—Todd E Manahan
*Assistant Examiner*—Christina D Gettman
(74) *Attorney, Agent, or Firm*—Squire, Sanders & Dempsey L.L.P.

(57) ABSTRACT

Patterns for polymeric radially expandable implantable medical devices such as stents for implantation into a bodily lumen are disclosed.

31 Claims, 6 Drawing Sheets

U.S. PATENT DOCUMENTS

| | | |
|---|---|---|
| 4,886,062 A | 12/1989 | Wiktor |
| 4,902,289 A | 2/1990 | Yannas |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,667,767 A | 9/1997 | Greff et al. |
| 5,667,796 A | 9/1997 | Otten |
| 5,670,558 A | 9/1997 | Onishi et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,780,807 A | 7/1998 | Saunders |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |
| 5,965,720 A | 10/1999 | Gryaznov et al. |
| 5,971,954 A | 10/1999 | Conway et al. |
| 5,976,182 A | 11/1999 | Cox |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,010,445 A | 1/2000 | Armini et al. |

| Patent Number | Date | Inventor |
|---|---|---|
| 6,015,541 A | 1/2000 | Greff et al. |
| 6,042,606 A * | 3/2000 | Frantzen .................... 623/1.18 |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,066,156 A | 5/2000 | Yan |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,083,258 A | 7/2000 | Yadav |
| 6,093,463 A | 7/2000 | Thakrar |
| 6,096,070 A | 8/2000 | Ragheb et al. |
| 6,096,525 A | 8/2000 | Patnaik |
| 6,099,562 A | 8/2000 | Ding et al. |
| 6,103,230 A | 8/2000 | Billiar et al. |
| 6,107,416 A | 8/2000 | Patnaik et al. |
| 6,110,188 A | 8/2000 | Narciso, Jr. |
| 6,113,629 A | 9/2000 | Ken |
| 6,117,979 A | 9/2000 | Hendriks et al. |
| 6,120,536 A | 9/2000 | Ding et al. |
| 6,120,904 A | 9/2000 | Hostettler et al. |
| 6,121,027 A | 9/2000 | Clapper et al. |
| 6,125,523 A | 10/2000 | Brown et al. |
| 6,127,173 A | 10/2000 | Eckstein et al. |
| 6,129,761 A | 10/2000 | Hubbell |
| 6,129,928 A | 10/2000 | Sarangapani et al. |
| 4,776,337 A | 11/2000 | Palmaz |
| 6,150,630 A | 11/2000 | Perry et al. |
| 6,153,252 A | 11/2000 | Hossainy et al. |
| 6,159,951 A | 12/2000 | Karpeisky et al. |
| 6,160,084 A | 12/2000 | Langer et al. |
| 6,165,212 A | 12/2000 | Dereume et al. |
| 6,166,130 A | 12/2000 | Rhee et al. |
| 6,169,170 B1 | 1/2001 | Gryaznov et al. |
| 6,171,609 B1 | 1/2001 | Kunz |
| 6,174,330 B1 | 1/2001 | Stinson |
| 6,177,523 B1 | 1/2001 | Reich et al. |
| 6,183,505 B1 | 2/2001 | Mohn, Jr. et al. |
| 6,187,045 B1 | 2/2001 | Fehring et al. |
| 6,206,911 B1 * | 3/2001 | Milo .................... 623/1.15 |
| 6,210,715 B1 | 4/2001 | Starling et al. |
| 6,224,626 B1 | 5/2001 | Steinke |
| 6,228,845 B1 | 5/2001 | Donovan et al. |
| 6,240,616 B1 | 6/2001 | Yan |
| 6,245,076 B1 | 6/2001 | Yan |
| 6,245,103 B1 | 6/2001 | Stinson |
| 6,248,344 B1 | 6/2001 | Ylanen et al. |
| 6,251,135 B1 | 6/2001 | Stinson et al. |
| 6,251,142 B1 | 6/2001 | Bernacca et al. |
| 6,273,913 B1 | 8/2001 | Wright et al. |
| 6,281,262 B1 | 8/2001 | Shikinami |
| 6,284,333 B1 | 9/2001 | Wang et al. |
| 6,287,332 B1 | 9/2001 | Bolz et al. |
| 6,290,721 B1 | 9/2001 | Heath |
| 6,293,966 B1 | 9/2001 | Frantzen |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 4,733,665 C2 | 1/2002 | Palmaz |
| 6,375,826 B1 | 4/2002 | Wang et al. |
| 6,379,381 B1 | 4/2002 | Hossainy et al. |
| 6,387,121 B1 | 5/2002 | Alt |
| 6,388,043 B1 | 5/2002 | Langer et al. |
| 6,395,326 B1 | 5/2002 | Castro et al. |
| 6,409,761 B1 | 6/2002 | Jang |
| 6,423,092 B2 | 7/2002 | Datta et al. |
| 6,436,132 B1 | 8/2002 | Patel et al. |
| 6,461,632 B1 | 10/2002 | Gogolewski |
| 6,464,720 B2 | 10/2002 | Boatman et al. |
| 6,479,565 B1 | 11/2002 | Stanley |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Wenz et al. |
| 6,511,748 B1 | 1/2003 | Barrows |
| 6,517,888 B1 | 2/2003 | Weber |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |
| 6,554,854 B1 | 4/2003 | Flanagan |
| 6,565,599 B1 | 5/2003 | Hong et al. |
| 6,569,191 B1 | 5/2003 | Hogan |
| 6,569,193 B1 | 5/2003 | Cox et al. |
| 6,572,649 B2 | 6/2003 | Berry et al. |
| 6,572,672 B2 | 6/2003 | Yadav et al. |
| 6,574,851 B1 | 6/2003 | Mirizzi |
| 6,585,755 B2 | 7/2003 | Jackson et al. |
| 6,592,614 B2 | 7/2003 | Lenker et al. |
| 6,592,617 B2 | 7/2003 | Thompson |
| 6,613,072 B2 | 9/2003 | Lau et al. |
| 6,626,939 B1 | 9/2003 | Burnside et al. |
| 6,635,269 B1 | 10/2003 | Jennissen |
| 6,645,243 B2 | 11/2003 | Vallana et al. |
| 6,656,162 B2 | 12/2003 | Santini, Jr. et al. |
| 6,664,335 B2 | 12/2003 | Krishnan |
| 6,666,214 B2 | 12/2003 | Canham |
| 6,667,049 B2 | 12/2003 | Janas et al. |
| 6,669,723 B2 | 12/2003 | Killion et al. |
| 6,676,697 B1 | 1/2004 | Richter |
| 6,679,980 B1 | 1/2004 | Andreacchi |
| 6,689,375 B1 | 2/2004 | Wahlig et al. |
| 6,695,920 B1 | 2/2004 | Pacetti et al. |
| 6,706,273 B1 | 3/2004 | Roessler |
| 6,709,379 B1 | 3/2004 | Brandau et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,746,773 B2 | 6/2004 | Llanos et al. |
| 6,752,826 B2 | 6/2004 | Holloway et al. |
| 6,753,007 B2 | 6/2004 | Haggard et al. |
| 6,764,505 B1 | 7/2004 | Hossainy et al. |
| 6,818,063 B1 | 11/2004 | Kerrigan |
| 6,846,323 B2 | 1/2005 | Yip et al. |
| 6,911,041 B1 * | 6/2005 | Zscheeg .................... 623/1.15 |
| 7,291,166 B2 | 11/2007 | Cheng et al. |
| 2001/0044652 A1 | 11/2001 | Moore |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0062148 A1 | 5/2002 | Hart |
| 2002/0065553 A1 | 5/2002 | Weber |
| 2002/0111590 A1 | 8/2002 | Davila et al. |
| 2002/0116050 A1 | 8/2002 | Kocur |
| 2002/0138133 A1 | 9/2002 | Lenz et al. |
| 2002/0161114 A1 | 10/2002 | Gunatillake et al. |
| 2003/0033001 A1 | 2/2003 | Igaki |
| 2003/0093107 A1 | 5/2003 | Parsonage et al. |
| 2003/0100865 A1 | 5/2003 | Santini, Jr. et al. |
| 2003/0105518 A1 | 6/2003 | Dutta |
| 2003/0105530 A1 | 6/2003 | Pirhonen |
| 2003/0171053 A1 | 9/2003 | Sanders |
| 2003/0187495 A1 | 10/2003 | Cully et al. |
| 2003/0208259 A1 | 11/2003 | Penhasi |
| 2003/0209835 A1 | 11/2003 | Chun et al. |
| 2003/0226833 A1 | 12/2003 | Shapovalov et al. |
| 2003/0236565 A1 | 12/2003 | Fifer |
| 2004/0088043 A1 * | 5/2004 | Klein .................... 623/1.16 |
| 2004/0093077 A1 | 5/2004 | White et al. |
| 2004/0098095 A1 | 5/2004 | Burnside et al. |
| 2004/0111149 A1 | 6/2004 | Stinson |
| 2004/0127970 A1 | 7/2004 | Weber |
| 2004/0143317 A1 | 7/2004 | Stinson et al. |

2004/0167610 A1   8/2004   Fleming III

FOREIGN PATENT DOCUMENTS

| | | |
|---|---|---|
| DE | 197 31 021 | 1/1999 |
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 544 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |
| GB | 2 247 696 | 3/1992 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/62710 | 10/2000 |
| WO | WO 00/64506 | 11/2000 |
| WO | WO 01/01890 | 1/2001 |
| WO | WO 03/057075 | 7/2003 |
| WO | WO 2004/019820 | 3/2004 |
| WO | WO 2004/023985 | 3/2004 |
| WO | WO 2004/062533 | 7/2004 |

OTHER PUBLICATIONS

U.S. Appl. No. 10/317,435, filed Dec. 11, 2002, Hossainy et al.
Anonymous, *Bioabsorbable stent mounted on a catheter having optical coherence tomography capabilities*, Research Disclosure, Sep. 2004, pp. 1159-1162.
Ansari, *End-to-end tubal anastomosis using an absorbable stent*, Fertility and Sterility, vol. 32(2), pp. 197-201 (Aug. 1979).
Ansari, *Tubal Reanastomosis Using Absorbable Stent*, International Journal of Fertility, vol. 23, No. 4, pp. 242-243 (1978).
Bull, *Parylene Coating for Medical Applications*, Medical Product Manufacturing News 18, 1 pg. (Mar. 1993).
Casper et al., *Fiber-Reinforced Absorbable Composite for Orthopedic Surgery*, Polymeric Materials Science and Engineering, 53: pp. 497-501 (1985).
Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).
Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).
Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).
Detweiler et al., *Sutureless Cholecystojejunostomu in Pigs Using an Absorbable Intraluminal Stent and Fibrin Glue*, Journal of Investigative Surgery, vol. 9(1), pp. 13-26 (Jan./Feb. 1996).
Devanathan et al., *Polymeric Conformal Coatings for Implantable Electronic Devices*, IEEE Transactions on Biomedical Engineering, vol. BME-27(11), pp. 671-675 (1980).
Elbert et al., *Conjugate Addition Reactions Combined with Free-Radical Cross-Linking for the Design of Materials for Tissue Engineering*, Biomacromolecules 2, pp. 430-441 (2001).
Hahn et al., *Biocompatibility of Glow-Discharge-Polymerized Films and Vacuum-Deposited Parylene*, J Applied Polymer Sci, 38, pp. 55-64 (1984).
Hahn et al., *Glow Discharge Polymers as Coatings for Implanted Devices*, ISA, pp. 109-111 (1981).
He et al., *Assessment of Tissue Blood Flow Following Small Artery Welding with a Intraluminal Dissolvable Stent*, Microsurgery, vol. 19(3), pp. 148-152 (1999).
Kelley et al., *Totally Resorbable High-Strength Composite Material*, Advances in Biomedical Polymers, 35, pp. 75-85 (1987).
Kubies et al., *Microdomain Structure In polylactide-block-poly(ethylene oxide) copolymer films*, Biomaterials 21, pp. 529-536 (2000).
Kutryk et al., *Coronary Stenting: Current Perspectives*, a companion to the Handbook of Coronary Stents pp. 1-16 (1999).
Martin et al., *Enhancing the biological activity of immobilized osteopontin using a type-1 collagen affinity coating*, J. Biomed. Mater Res 70A, pp. 10-19 (2004).
Mauduit et al., *Hydrolytic degradation of films prepared from blends of high and low molecular weight poly(DL-lactic acid)s*, J. Biomed. Mater. Res. v. 30, pp. 201-207 (1996).
Middleton et al., *Synthetic biodegradable polymers as orthopedic devices*, Biomaterials, vol. 21, pp. 2335-2346 (2000).
Muller et al., *Advances in Coronary Angioplasty: Endovascular Stents*, Coron. Arter. Dis., 1(4), pp. 438-448 (Jul./Aug. 1990).
Nichols et al., *Electrical Insulation of Implantable Devices by Composite Polymer Coatings*, ISA Transactions, 26(4), pp. 15-18 (1987).
Peuster et al., *A novel approach to temporary stenting: degradable cardiovascular stents produced from corrodible metal-results 6-18 months after implantation into New Zealand white rabbits*, Heart 86, pp. 563-569 (2001).
Pietrzak et al., *Bioabsorbable Fixation Devices: Status for the Craniomaxillofacial Surgeon*, J. Craniofaxial Surg. 2, pp. 92-96 (1997).
Pietrzak et al., *Bioresorbable implants—practical considerations*, Bone vol. 19, No. 1, Supplement Jul. 1996: 109S-119S.
Redman, *Clinical Experience with Vasovasostomy Utilizing Absorbable Intravasal Stent*, Urology, vol. 20(1), pp. 59-61 (Jul. 1982).
Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).
Schatz, *A View of Vascular Stents*, Circulation, 79(2), pp. 445-457 (Feb. 1989).
Schmidt et al., *Long-Term Implants of Parylene-C Coated Microelectrodes*, Med & Biol Eng & Comp, 26(1), pp. 96-101 (Jan. 1988).
Spagnuolo et al., *Gas 1 is induced by VE-cadherin and vascular endothelial growth factor and inhibits endothelial cell apoptosis*, Blood 103, pp. 3005-3012 (2004).
Tamai et al., *Initial and 6-Month Results of Biodegradable Poly-I-Lactic Acid Coronary Stents in Humans*, Circulation, pp. 399-404 (Jul. 25, 2000).
Tsuji et al., *Biodegradable Polymeric Stents*, Current Interventional Cardiology Reports 3, pp. 10-17 (2001).
Völkel et al., *Targeting of immunoliposomes to endothelial cells using a single -chain Fv fragment directed against human endoglin(CD105)*, Biochimica et Biophysica Acta 1663, pp. 158-166 (2004).
Von Recum et al., *Degradation of polydispersed poly(L-lactic acid) to modulate lactic acid release*, Biomaterials 16, pp. 441-445 (1995).
Yau et al., Modern Size-Exclusion Liquid Chromatography, Wiley-Interscience Publication, IX-XV (1979).

* cited by examiner

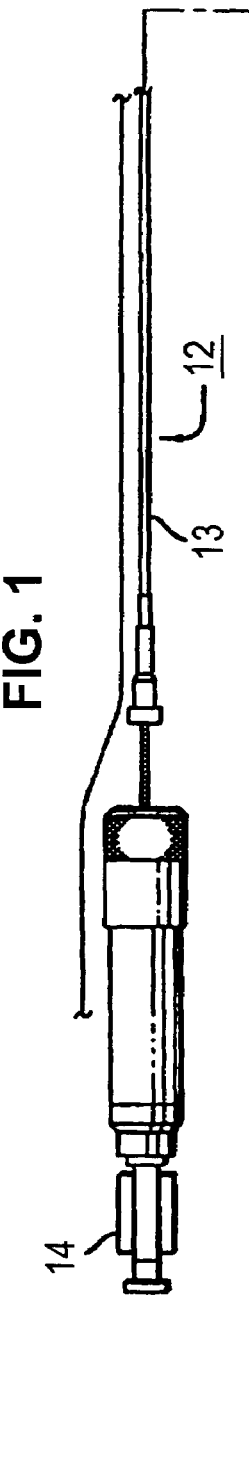
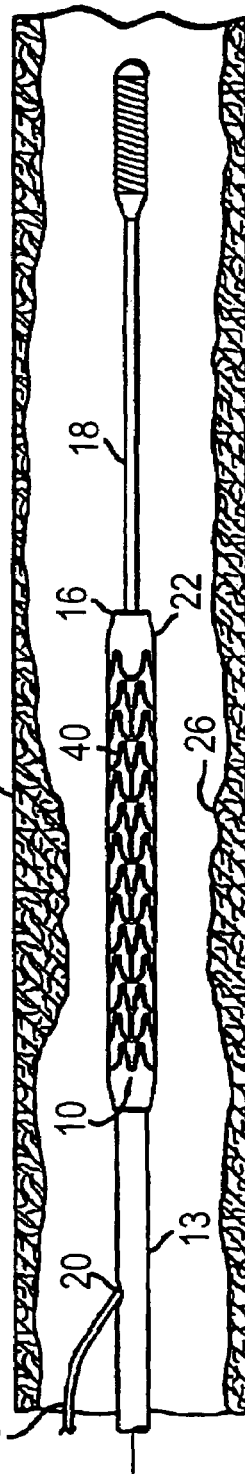
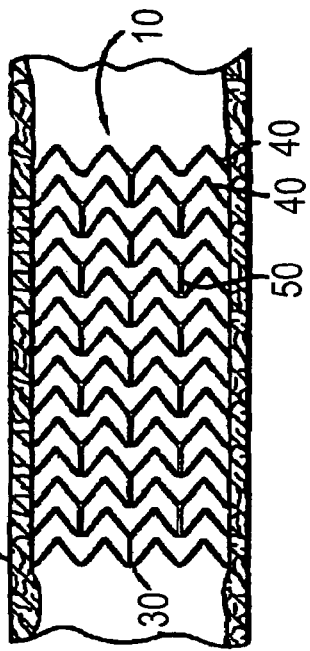
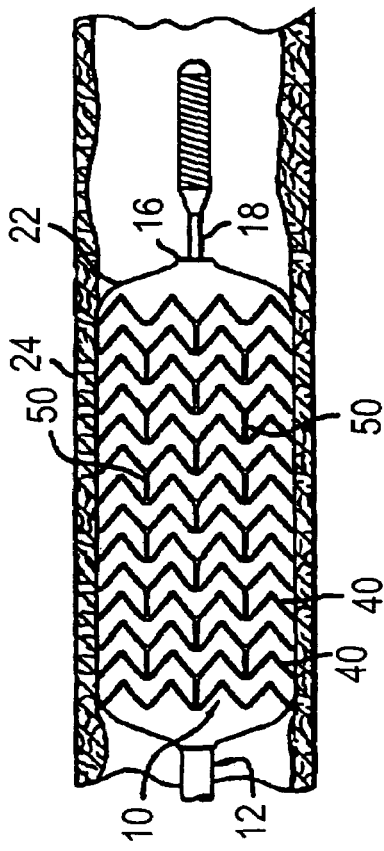
FIG. 1
FIG. 2
FIG. 3

POLYMERIC STENT PATTERNS

BACKGROUND OF THE INVENTION

1. Field of the Invention

This invention relates to radially expandable implantable medical devices such as stents for implantation into a bodily lumen. In particular, the invention relates to stent patterns for polymeric stents.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil.

In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other. Thus, a stent pattern may be designed to meet the mechanical requirements of a stent described above which include radial strength, minimal recoil, and flexibility.

Stents have been made of many materials such as metals and polymers, including biodegradable polymer materials. Biodegradable stents are desirable in many treatment applications in which the presence of a stent in a body may be necessary for a limited period of time until its intended function of, for example, maintaining vascular patency and/or drug delivery is accomplished. A stent for drug delivery or a medicated stent may be fabricated by coating the surface of either a metallic or polymeric scaffolding with a polymeric carrier that includes an active agent or drug. An agent or drug may also be mixed or dispersed within the polymeric scaffolding.

In general, there are several important aspects in the mechanical behavior of polymers that affect stent design. Polymers tend to have lower strength than metals on a per unit mass basis. Therefore, polymeric stents typically have less circumferential strength and radial rigidity than metallic stents. Inadequate radial strength potentially contributes to a relatively high incidence of recoil of polymeric stents after implantation into vessels.

Another potential problem with polymeric stents is that their struts or bar arms can crack during crimping and expansion, especially for brittle polymers. The localized portions of the stent pattern subjected to substantial deformation tend to be the most vulnerable to failure. Furthermore, in order to have adequate mechanical strength, polymeric stents may require significantly thicker struts than a metallic stent, which results in an undesirably larger profile.

Another potential problem with polymeric stents is long term creep. Long term creep is typically not an issue with metallic stents. Long term creep refers to the gradual deformation that occurs in a polymeric material subjected to an applied load. Long term creep occurs even when the applied load is constant. Long term creep in a polymeric stent reduces the effectiveness of a stent in maintaining a desired vascular patency. In particular, long term creep allows inward radial forces to permanently deform a stent radially inward.

Therefore, it would be desirable to have polymeric stents with stent patterns that provide adequate radial strength, minimal recoil, and flexibility.

SUMMARY OF THE INVENTION

Certain embodiments of the present invention include a radially expandable intravascular stent for implanting in a bodily lumen. The stent may include a plurality of pairs of radially expandable undulating cylindrical rings that are longitudinally aligned and are connected at a plurality of intersections to form a plurality of hour-glass shaped cells. Each ring may have a first delivery diameter and a second implanted diameter. A first ring of the pair may include two v-shaped undulations with peaks between each intersection. The v-shaped undulations may include long bar arms connected at each intersection, a short bar arm connected to each long bar arm, and a linear or curved bar arm connecting the two short bar arms of each v-shaped undulation. A second ring of the pair may include two v-shaped undulations with valleys between each intersection. The v-shaped undulation may include a long bar arm connected at the intersection, a short bar arm connected to each long bar arm, and a linear or curved bar arm connecting the two short bar arms of each v-shaped undulation. The stent may further include a plurality of links comprising linear bar arms connecting adjacent rings such that at least one link joins an intersection of the plurality of intersections of a pair of one ring with a linear or curved bar arm of an adjacent ring.

Further embodiments of the present invention include a radially expandable intravascular stent for implanting in a bodily lumen having a plurality of radially expandable undulating cylindrical rings that are longitudinally aligned. Each ring may have a first delivery diameter and a second implanted diameter and a plurality of interconnected cells. Each cell may be formed by two opposing M-shaped elements aligned circumferentially and connected at each end of the elements to form an hour-glass shape. Each M-shaped element may include a long linear bar arm at one end connected to a short linear bar arm and a linear or curved bar arm connecting the short bar arms. The stent may also include a plurality of links connecting adjacent cylindrical rings such that at least one link connects a connection point of two opposing M-shaped elements on one ring with a linear or curved bar arm of an adjacent ring.

Additional embodiments of the present invention may include a radially expandable intravascular stent for implanting in a bodily lumen having a plurality of pairs of radially expandable undulating cylindrical rings that are longitudinally aligned. A first ring of the pair may include adjacent pairs of first v-shaped sections with peaks formed by a long linear bar arm and a short linear bar arm of the first ring. The short linear bar arms of the first ring may be connected by a linear or curved bar arm of the first ring. The adjacent pairs of first v-shaped sections may be separated by a second v-shaped section with a valley formed by the long linear bar arms. A second ring of the pair of rings may include adjacent pairs of third v-shaped sections with valleys formed by a long linear bar arm and a short linear bar arm of the second ring, the short linear bar arms of the second ring are connected by a linear or curved bar arm of the second ring. The adjacent pairs of third v-shaped sections may be separated by a fourth v-shaped undulation with a peak formed by the long linear bar arms of the second ring. The first ring and the second ring may intersect at the valleys of the second v-shaped undulation of the first ring and the peaks of the v-shaped undulation of the second ring to form an hourglass shape between the pairs of rings. The stent may also include at least one link connecting the intersection of a pair of rings with a short linear or curved bar arm of an adjacent pair of rings.

Other embodiments of the present invention include a radially expandable intravascular stent for implanting in a bodily lumen having a plurality of radially expandable undulating cylindrical rings that are longitudinally aligned. Each ring may have a first delivery diameter and a second implanted diameter and a plurality of interconnected cells. Each cell may include two adjacent parallelogram-shaped regions. Each region may be open at one end opposite a vertex such that the open ends are opposing. The cells may be connected circumferentially at an intersection at the vertices opposite the open ends. The axes along the vertices adjacent the open ends of each region may be parallel or substantially parallel to a longitudinal axis of the stent. Each region may include two long bar arms, two short bar arms, and two curved or linear bar arms. The long bar arms may be in a v-configuration connected at an adjacent cell at a vertex of the v-configuration. A longitudinal axis of the stent may be perpendicular to a line through the vertices of the v-configurations of the two parallelogram-shaped regions. Each of two short bar arms of the short bar arms may be connected at one end to the long bar arms. The two curved or linear bar arms may connect the opposing regions such that each connect ends of the short bar arms in the different regions. The stent may also include a plurality of links connecting adjacent cylindrical rings such that at least one link connects an intersection of circumferentially adjacent cells on one ring with a linear or curved bar arm of a longitudinally adjacent ring.

Another embodiment of the present invention includes a radially expandable intravascular stent for implanting in a bodily lumen having a plurality of pairs of radially expandable undulating cylindrical rings that are longitudinally aligned and are connected at a plurality of intersections on each pair by a plurality of first bar arms aligned parallel or substantially parallel to a longitudinal axis of the stent, each ring having a first delivery diameter and a second implanted diameter. A first ring of each pair may include a peak between two valleys between the intersections of the first bar arms with the first ring. The peak may be formed by two long bar arms and each of the valleys may be formed by one of the long bar arms and a short bar arm. A second ring of each pair may include a valley between two peaks between the intersections of the first bar arms with the second ring. The valley may be formed by two long bar arms and the peaks may be formed by one of the long bar arms and a short bar arm. The first bar arms may connect short bar arms of the first ring of the pairs to short bar arms of the second ring of the pairs at the intersections. The stent may further include at least one second bar arm connecting a peak of a first ring of a pair to a valley of a second ring of an adjacent pair of rings.

Certain additionally embodiments of the present invention may include a radially expandable intravascular stent for implanting in a bodily lumen having a plurality of pairs of radially expandable undulating cylindrical rings that are longitudinally aligned, such that a first ring of the pair comprises peaks formed by long linear bar arms alternating with peaks formed by short linear bar arms and valleys in between the peaks formed by short and long linear bar arms and a second ring of the pair comprises valleys formed by long linear bar arms alternating with valleys formed by short linear bar arms and peaks in between the valleys formed by short and long linear bar arms. The peak formed by the short bar arms of the first ring may be connected to a valley formed by the short bar arms of the second ring by a longitudinally aligned first bar arm. The stent may include a plurality of longitudinally aligned second bar arms connecting the peaks formed by the long bar arms of first ring to the valleys formed by the long bar arms of the second ring of an adjacent pair of rings.

BRIEF DESCRIPTION OF THE DRAWINGS

FIG. 1 is an elevation view, partially in section, of a stent which is mounted on a rapid-exchange delivery catheter and positioned within an artery.

FIG. 2 is an elevation view, partially in section, similar to that shown in FIG. 1, wherein the stent is expanded within the artery so that the stent embeds within the arterial wall.

FIG. 3 is an elevation view, partially in section, showing the expanded stent implanted within the artery after withdrawal of the rapid-exchange delivery catheter.

DETAILED DESCRIPTION OF THE INVENTION

Figure 4:
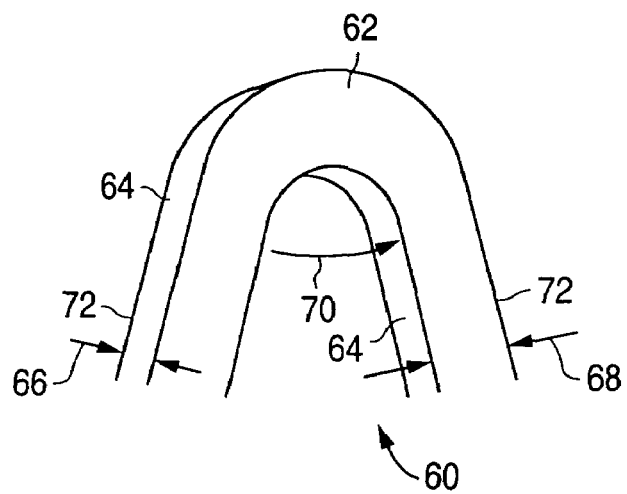
FIG. 4 depicts a curved portion of a stent.

For the purposes of the present invention, the following terms and definitions apply:

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

Furthermore, a property of a material that quantifies a degree of strain with applied stress is the modulus. "Modulus" may be defined as the ratio of a component of stress or force per unit area applied to a material divided by the strain along an axis of applied force that results from the applied force. For example, a material has both a tensile and a compressive modulus. A material with a relatively high modulus tends to be stiff or rigid. Conversely, a material with a relatively low modulus tends to be flexible. The modulus of a material depends on the molecular composition and structure, temperature of the material, and the strain rate or rate of deformation. For example, below its $T_g$, a polymer tends to be brittle with a high modulus. As the temperature of a polymer is increased from below to above its $T_g$, its modulus decreases.

The "ultimate strength" or "strength" of a material refers to the maximum stress that a material will withstand prior to fracture. A material may have both a tensile and a compressive strength. The ultimate strength may be calculated from the maximum load applied during a test divided by the original cross-sectional area.

The term "elastic deformation" refers to deformation of an object in which the applied stress is small enough so that the object moves towards its original dimensions or essentially its original dimensions once the stress is released. However, an elastically deformed polymer material may be prevented from returning to an undeformed state if the material is below the $T_g$ of the polymer. Below $T_g$, energy barriers may inhibit or prevent molecular movement that allows deformation or bulk relaxation.

"Elastic limit" refers to the maximum stress that a material will withstand without permanent deformation. The "yield point" is the stress at the elastic limit and the "ultimate strain" is the strain at the elastic limit. The term "plastic deformation" refers to permanent deformation that occurs in a material under stress after elastic limits have been exceeded.

Various embodiments of stent patterns for polymeric stents are disclosed herein. Stents may be composed partially or completely of polymers. In general, polymers can be biostable, bioabsorbable, biodegradable, or bioerodable. Biostable refers to polymers that are not biodegradable. The terms biodegradable, bioabsorbable, and bioerodable, as well as degraded, eroded, and absorbed, are used interchangeably and refer to polymers that are capable of being completely eroded or absorbed when exposed to bodily fluids such as blood and can be gradually resorbed, absorbed and/or eliminated by the body.

A stent made from a biodegradable polymer is intended to remain in the body for a duration of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain. In some embodiments, very negligible traces or residue may be left behind. The duration can be in a range from about a month to a few years. However, the duration is typically in a range from about six to twelve months.

The general structure and use of stents will be discussed first in order to lay a foundation for the embodiments of stent patterns herein. In general, stents can have virtually any structural pattern that is compatible with a bodily lumen in which it is implanted. Typically, a stent is composed of a pattern or network of circumferential rings and longitudinally extending interconnecting structural elements of struts or bar arms. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, expansion ratio or coverage area, and longitudinal flexibility.

FIGS. 1-3 can represent any balloon expandable stent 10 with which the various configurations can be used. FIG. 1 depicts a stent 10 with interconnected cylindrical rings 40 mounted on a catheter assembly 12 which is used to deliver stent 10 and implant it in a bodily lumen. Rings 40 are connected by links 50.

For example, a bodily lumen may include a coronary artery, peripheral artery, or other vessel or lumen within the body. The catheter assembly includes a catheter shaft 13 which has a proximal end 14 and a distal end 16. The catheter assembly is configured to advance through the patient's vascular system by advancing over a guide wire by any of the well-known methods of an over-the-wire system (not shown) or a well-known rapid exchange catheter system, such as the one shown in FIG. 1. The stent 10 in FIGS. 1-3 conceptually represents any type of stent well-known in the art, i.e., one having a plurality of cylindrical rings 40.

Catheter assembly 12, as depicted in FIG. 1, includes an RX (rapid-exchange) port 20 where the guide wire 18 exits the catheter. The distal end of guide wire 18 exits catheter distal end 16 so that the catheter advances along the guide wire on a section of the catheter between RX port 20 and catheter distal end 16. As is known in the art, the guide wire lumen which receives the guide wire is sized for receiving various diameter guide wires to suit a particular application.

The stent is mounted on an expandable member 22 (e.g., a balloon) and is crimped tightly thereon, so that the stent and expandable member present a low profile diameter for delivery through the arteries.

As shown in FIG. 1, a partial cross-section of an artery 24 has a small amount of plaque that has been previously treated by angioplasty or other repair procedure. Stent 10 is used to repair a diseased or damaged arterial wall as shown in FIG. 1, or a dissection, or a flap, all of which are commonly found in the coronary arteries and other vessels. Stent 10, and embodiments of the stents described herein, also can be placed and implanted without any prior angioplasty.

In a typical procedure to implant stent 10, guide wire 18 is advanced through the patient's vascular system by well-known methods, so that the distal end of the guide wire is advanced past the plaque or a diseased area 26. Prior to implanting the stent, the cardiologist may wish to perform an angioplasty or other procedure (i.e., atherectomy) in order to open and remodel the vessel and the diseased area. Thereafter, stent delivery catheter assembly 12 is advanced over the guide wire so that the stent is positioned in the target area. The expandable member or balloon 22 is inflated by well-known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIGS. 2 and 3, the balloon is fully inflated with the stent expanded and pressed against the vessel wall. In FIG. 3, the implanted stent remains in the vessel after the balloon has been deflated and the catheter assembly and guide wire have been withdrawn from the patient.

Stent 10 holds open the artery after the catheter is withdrawn, as illustrated by FIG. 3. A stent may be formed from a cylindrical tube with a constant wall thickness, so that the straight and undulating or curved components of the stent are relatively flat in transverse cross-section. Thus, when the stent is expanded, a flat abluminal surface is pressed into the wall of the artery. As a result, the stent does not interfere with the blood flow through the artery. After the stent is pressed into the wall of the artery, it eventually becomes covered with endothelial cell growth which further minimizes blood flow interference. The undulating or curved portion of the stent provides good tacking characteristics to prevent stent movement within the artery. Because cylindrical rings 40 are closely spaced at regular intervals, they provide uniform support for the wall of the artery. Consequently the rings are well adapted to tack up and hold in place small flaps or dissections in the wall of the artery.

In general, a stent pattern is designed so that the stent can be radially expanded (to allow deployment). The stresses involved during expansion from a low profile to an expanded profile are generally distributed throughout various structural elements of the stent pattern. As a stent expands, various portions of the stent can deform to accomplish a radial expansion.

FIG. 4 depicts a curved portion 60 of a stent. Portion 60 has an abluminal surface 62 and an opposing luminal surface (not shown). Sidewall surfaces 64 are also shown. Portion 60 has a radial thickness 66 and a strut width 68. Stent patterns typically have a constant radial thickness throughout the pattern because stents are typically fabricated from tubes of sheets of uniform or substantially uniform thickness. When a stent undergoes radial expansion, portions of some struts bend resulting in an increase of an angle 70 between straight arms 72.

The stiffness or flexibility of a portion of a stent pattern can depend on the mass of the portion of the stent. The mass of a portion may be varied by varying the width and/or length of strut or bar arm that makes up a portion. The shorter a strut, the less stiff and more flexible it is. Similarly, the smaller the width of a stent, the less stiff and more flexible it is. In addition, a portion with a smaller mass may tend to undergo more deformation. By allocating the amount of mass to specific struts, it is possible to create a stent having variable strength with greater strength at the high mass areas.

In addition, deformation of portions of a stent during radial expansion can also influence a stent's radial strength, recoil, and flexibility. In general, deformation of a polymeric material may induce alignment or increase the degree of molecular orientation of polymer chains along a direction of applied stress. Molecular orientation refers to the relative orientation of polymer chains along a longitudinal or covalent axis of the polymer chains. A polymer with a high degree of molecular orientation has polymer chains that are aligned or close to being aligned along their covalent axes.

Polymers in the solid state may have amorphous regions and crystalline regions. Crystalline regions include highly oriented polymer chains in an ordered structure. An oriented crystalline structure tends to have high strength and high modulus (low elongation with applied stress) along an axis of alignment of polymer chains.

On the other hand, amorphous polymer regions include relatively disordered polymer chains that may or may not be oriented in a particular direction. However, a high degree of molecular orientation may be induced by applied stress even in an amorphous region. Inducing orientation in an amorphous region also tends to increase strength and modulus along an axis of alignment of polymer chains. Additionally, for some polymers under some conditions, induced alignment in an amorphous polymer may be accompanied by crystallization of the amorphous polymer into an ordered structure. This is referred to as strain-induced crystallization.

Rearrangement of polymer chains may take place when a polymer is stressed in an elastic region and in a plastic region of the polymer material. A polymer stressed beyond its elastic limit to a plastic region generally retains its stressed configuration and corresponding induced polymer chain alignment when stress is removed. The polymer chains may become oriented in the direction of the applied stress which results in an oriented structure. Thus, induced orientation in portions of a stent may result in a permanent increase in strength and modulus in that portion. This is particularly advantageous since after expansion in a lumen, it is generally desirable for a stent to remain rigid and maintain its expanded shape so that it may continue to hold open the lumen.

Therefore, radial expansion of a stent may result in deformation of localized portions. The deformation of the localized portions may induce a high degree of molecular orientation and possibly crystallization in the localized portions in the direction of the stress. Thus, the strength and modulus in such localized portions may be increased. The increase in strength of localized portions may increase the radial strength and rigidity of the stent as a whole. The amount of increase in radial strength of a stent may depend upon the orientation of the stress in the localized portions relative to the circumferential direction. If the deformation is aligned circumferentially, for example, the radial strength of the expanded stent can be increased due to the induced orientation and possibly strain induced crystallization of the localized portions. Thus, plastic deformation of localized portions may cause the portions to be "locked" in the deformed state.

Furthermore, induced orientation and crystallization of a portion of a stent may increase a $T_g$ of at least a deformed portion. The $T_g$ of the polymer in the device may be increased to above body temperature. Therefore, barriers to polymer chain mobility below $T_g$ inhibit or prevent loss of induced orientation and crystallization. Thus, a deformed portion may have a high creep resistance and may more effectively resist radial compressive forces and retain the expanded shape during a desired time period.

Figure 5:
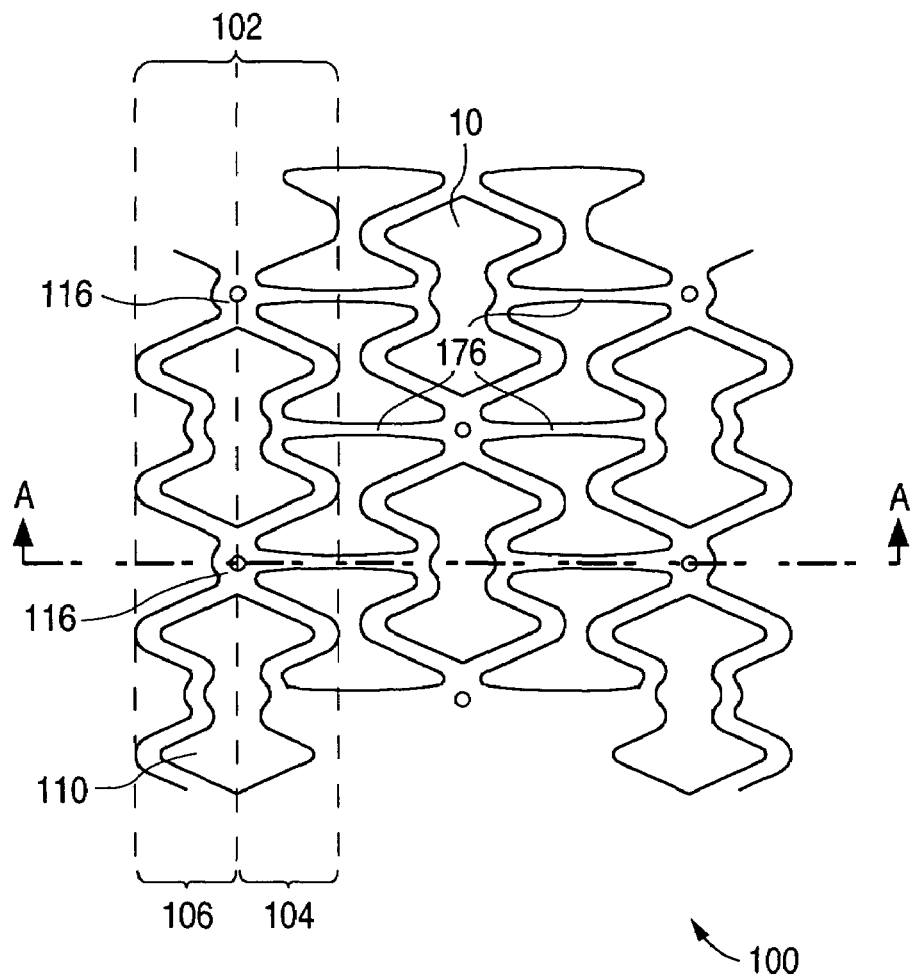
FIG. 5 depicts a stent pattern.

FIG. 5 depicts one embodiment of a stent pattern. In FIG. 5, a portion of a stent pattern 100 is shown in a flattened condition so that the pattern can be clearly viewed. When the flattened portion of stent pattern 100 is in a cylindrical condition, it forms a radially expandable stent. The stent is typically formed from a tubular member, but it can be formed from a flat sheet such as the portion shown in FIG. 5 and rolled and bonded into a cylindrical configuration.

FIG. 5 depicts three pairs 102 of undulating cylindrical rings 104 and 106. Pairs 102 form a ring of hour-glass-shaped cells or regions 110. Embodiments of stent 100 may have any number of pairs 102 of rings. For reference, line A-A represents the longitudinal axis of a stent using the pattern depicted in FIG. 5. A portion of stent 100 in FIG. 5 is shown in greater detail in FIG. 6.

Figure 6:
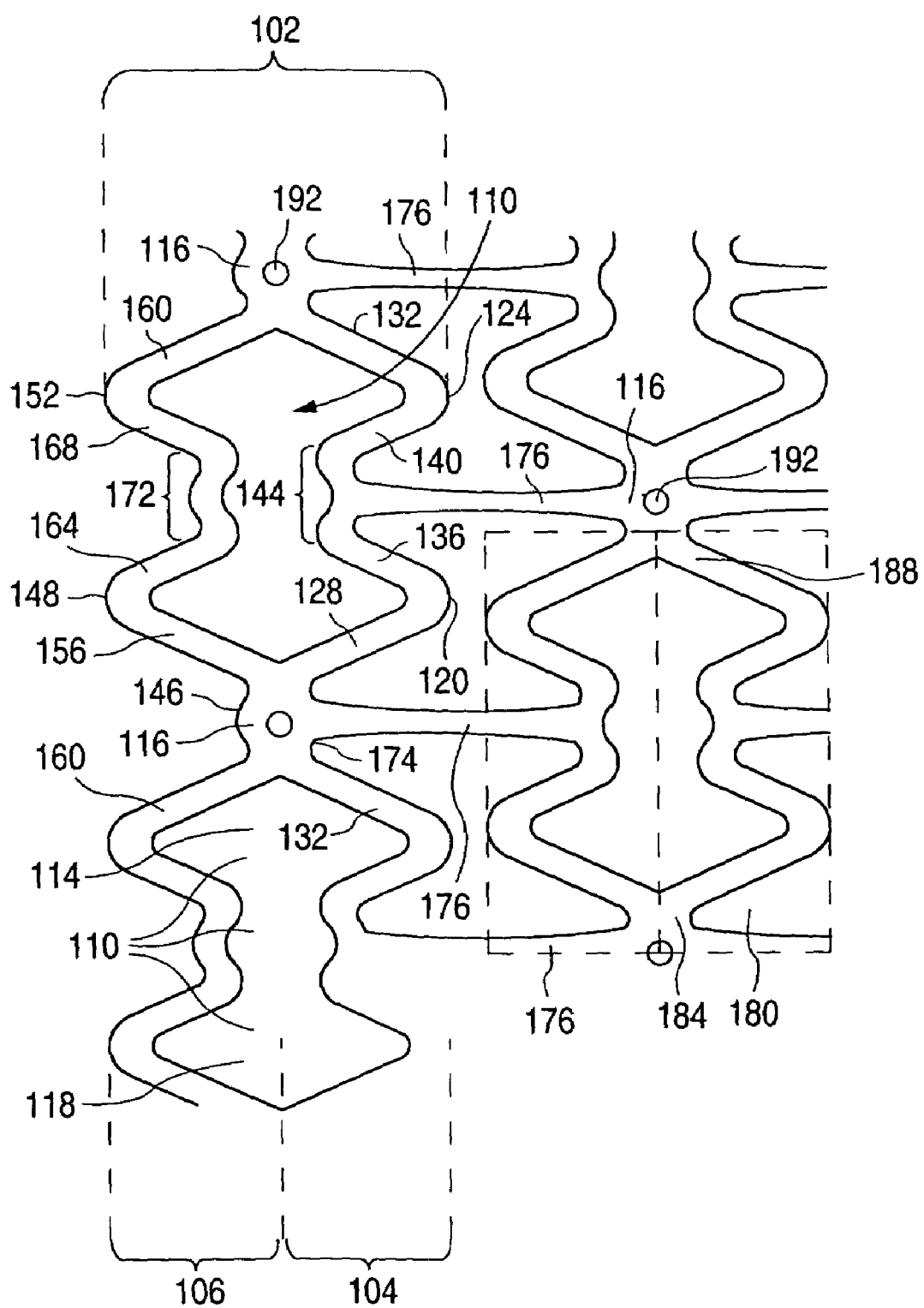
FIG. 6 depicts a portion of the stent pattern from FIG. 5.

As depicted in FIG. 6, pairs 102 of radially expandable undulating cylindrical rings 104 and 106 are longitudinally aligned and are connected at a plurality of intersections 116 to form a plurality of hour-glass-shaped cells 110. Hour-glass-shaped cells 110 may be described in part as having two adjacent parallelogram-shaped regions 114 and 118. Each of regions 114 and 118 is open at one end opposite a vertex such that the open ends are opposing. The axes along the vertices adjacent the open ends of each region are parallel or substantially parallel to a longitudinal axis of the stent. Embodiments of the stent depicted in FIG. 5 can include any number of adjacent parallelogram-shaped regions or cells along a circumferential direction and rings along the longitudinal axis.

Rings 104 of pairs 102 include two v-shaped undulations with peaks 120 and 124 between each intersection 116. The v-shaped undulations include long bar arms 128 and 132 connected at intersections 116, short bar arms 136 and 140 connected to long bar arms 128 and 132, and a linear or curved bar arm 144 connecting short bar arms 136 and 140 of each v-shaped undulation. A valley 146 at intersection 116 formed by long bar arms 128 and 132 is positioned between consecutive v-shaped undulations with peaks 120 and 124.

Rings 106 of pairs 102 include two v-shaped undulations with valleys 148 and 152 between each intersection 116. The v-shaped undulations include long bar arms 156 and 160 connected at the intersections 116, short bar arms 164 and 168 connected to long bar arms 156 and 160, and a linear or curved bar arm 172 connecting short bar arms 164 and 168 of each v-shaped undulation. A valley 174 at intersection 116 formed by long bar arms 156 and 160 is positioned between consecutive v-shaped undulations with peaks 148 and 152.

As shown in FIG. 6, stent 100 can also be described as a plurality of interconnected cells 110 formed by two opposing M-shaped elements 176 and 180 aligned circumferentially and connected at opposing ends 184 and 188 of elements 176 and 180 to form hour-glass-shaped cells 110. M-shaped elements have long linear bar arms at one end connected to short linear bar arms, and a linear or curved bar arm connecting the short bar arms.

As shown in FIGS. 5 and 6, stent 100 has a plurality of links including linear bar arms 176 connecting adjacent rings. Linear bar arm 176 connects an intersection 116 with a linear or curved bar arm of an adjacent ring. FIGS. 5 and 6 show that intersections 116 can be a junction of six bar arms: two linking bar arms and four long bar arms of the hour-glass-shaped cells. Such an intersection enhances the geometric stability of the stent.

Some embodiments of the stent in FIGS. 5 and 6 may include holes or depots 192 to accommodate radiopaque material. The stent may be visualized during delivery and deployment using X-Ray imaging if it contains radiopaque materials. By looking at the position of stent with respect to the treatment region, the stent may be advanced with the catheter to a location. In one embodiment, depots or holes may be drilled using a laser.

As indicated above, expansion of a stent tends to result in substantial deformation in localized portions of the stent pattern. Such deformation can result in induced polymer chain alignment and possibly strain induced crystallization, which may tend to increase the strength and modulus of these portions. When a stent having a pattern such as those depicted in FIGS. 5 and 6 is expanded, the hour-glass-shaped cells tend to become narrower along the longitudinal axis and longer along the circumferential direction.

As depicted in FIGS. 5 and 6, the short bar arms are shorter than long bar arms. The short bar arms tend to plastically deform prior to the long bar arms upon expansion. As discussed, above, the smaller the mass of a bar arm, the more readily it deforms under an applied stress. As stent 100 is expanded, short bar arms may tend to circumferentially align and become plastically deformed along their length. Therefore, the shorter bar arms may become permanently deformed or locked and rigid and act to provide resistance against recoil and inward radial forces.

Long bar arms, however, may tend to have a lower degree of circumferential alignment. As a result, the deformation of the longer bar arms may be completely or substantially elastic. Thus, the longer bar arms tend to be relatively elastic and provide flexibility to the stent. As indicated above, such flexibility is desirable due to cyclic forces imposed on the stent. Such flexibility is important in preventing cracking of the stent.

Also, the width of the bar arms may also be varied to control the amount of plastic deformation in the bar arms. As indicated above, the thinner the bar arm, the more it deforms under an applied stress.

Radial expansion of the stent pattern in FIGS. 5 and 6 causes hour-glass-shaped cells 110 to become narrower along the longitudinal axis. Substantial local deformation tends to occur at intersections 116 where hour-glass-shaped cells 110 are connected along cylindrical rings. Deformation also occurs at peaks and valleys due to a change in angle between short bar arms and long bar arms and between two long bar arms, e.g., long bar arm 128 and short bar arm 136; long bar arm 132 and short bar arm 140; and long bar arm 128 and long bar arm 156. As indicated above, plastic deformation occurs along the length of the short bar arms which tends to increase the radial strength of the stent and reduce recoil. Additionally, the strain-induced crystallization can reduce long term creep in the stent.

In a similar manner, crimping causes the hour-glass-shaped cells to become wider along the longitudinal axis and longer along the circumferential direction. Substantial deformation also occurs in the peaks and valleys.

Figure 7:
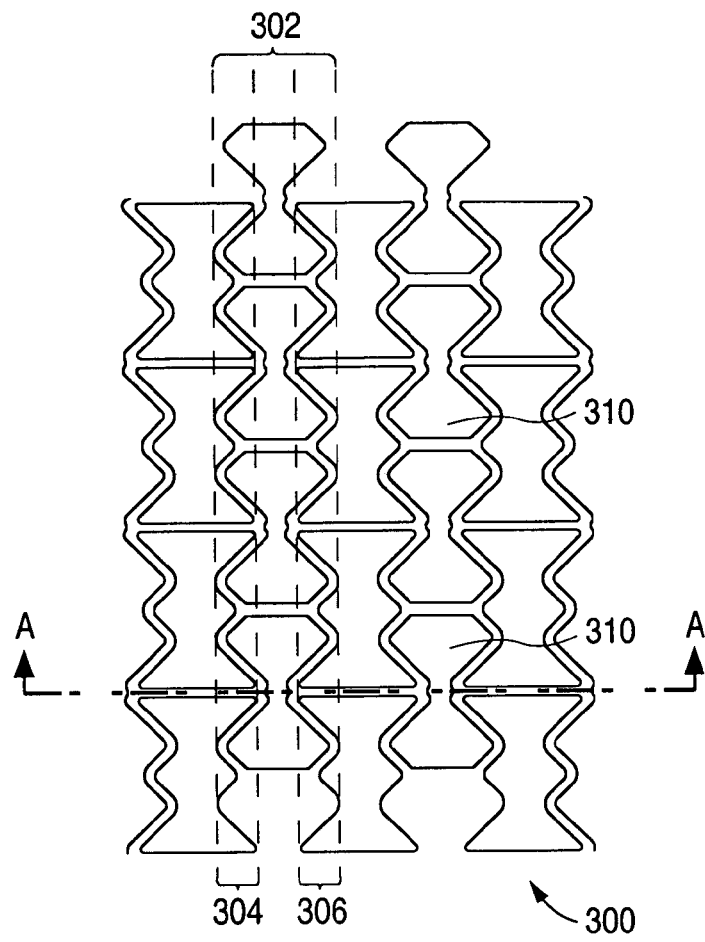
FIG. 7 depicts a stent pattern.
Figure 9:
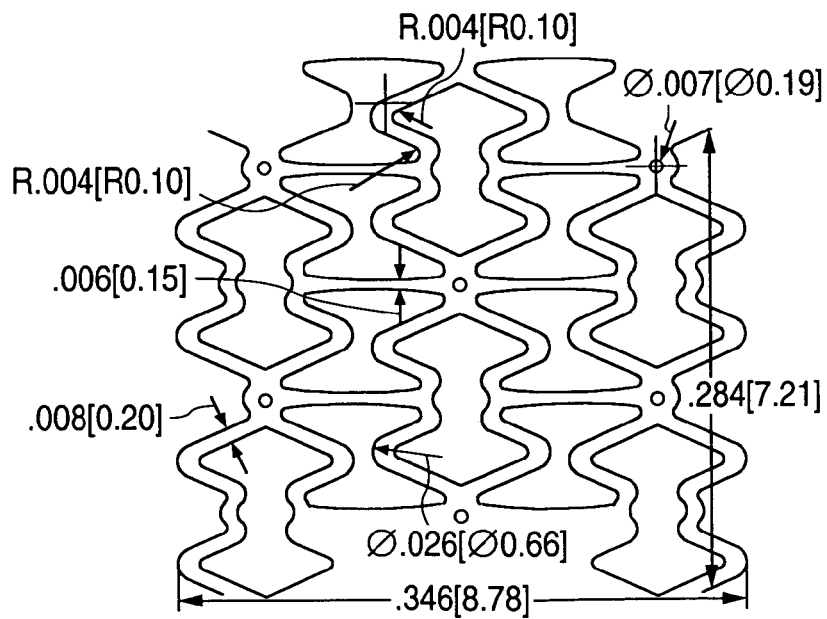
FIG. 9 depicts an embodiment of the dimensions of stent 100 of FIG. 5.

FIGS. 7 and 9 depict another embodiment of a stent pattern. In FIG. 7, a portion of a stent pattern 300 is also shown in a flattened condition so that the pattern can be clearly viewed.

When the flattened portion of stent pattern 300 is in a cylindrical configuration, it forms a radially expandable stent.

FIG. 7 depicts three pairs 302 of undulating cylindrical rings 304 and 306. Pairs 302 form a ring of bow-tie-shaped cells or regions 310. Embodiments of stent 300 may have any number of pairs 302 of rings. For reference, line A-A represents the longitudinal axis of stent 300. A portion of stent 300 in FIG. 7 is shown in greater detail in FIG. 8.

Figure 8:
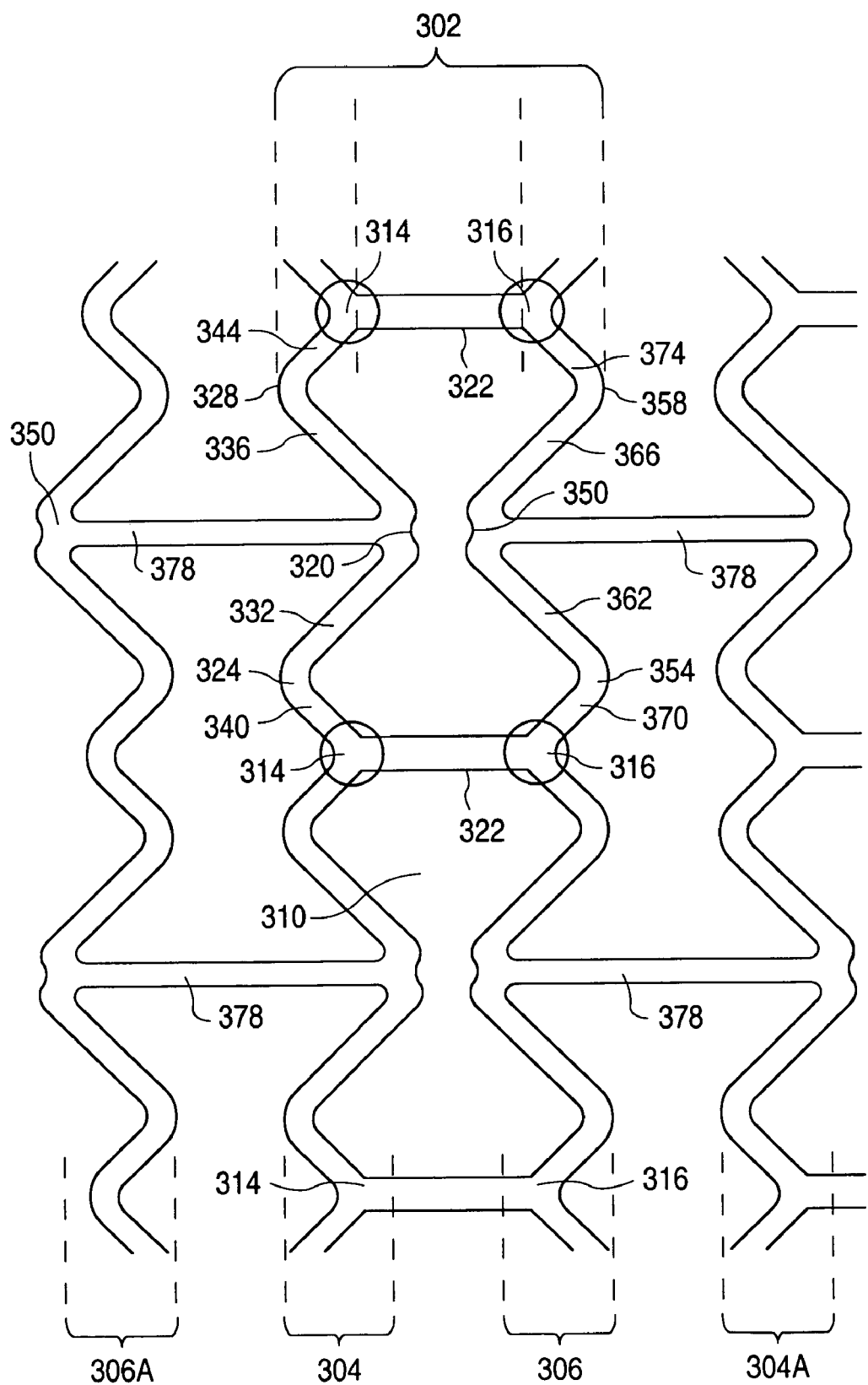
FIG. 8 depicts a portion of the stent pattern from FIG. 8.

As depicted in FIG. 8, pairs 302 of radially expandable undulating cylindrical rings 304 and 306 are longitudinally aligned and are connected at a plurality of intersections 314 and 316 by a plurality of first bar arms 322 to form a plurality of bow-tie-shaped cells 310. First bar arms 322 are aligned parallel or substantially parallel to the longitudinal axis of stent 300.

Ring 304 of pairs 302 include a peak 320 between two valleys 324 and 328 between intersections 314. Peak 320 is formed by two long bar arms 332 and 336. Valley 324 is formed by long bar arm 332 and a short bar arm 340 and valley 328 is formed by long bar arm 336 and a short bar arm 344.

Ring 306 of pairs 302 include a valley 350 between two peaks 354 and 358 between intersections 316. Valley 350 is formed by two long bar arms 362 and 366. Peak 354 is formed by long bar arm 362 and a short bar arm 370 and peak 358 is formed by long bar arm 366 and a short bar arm 374. First bar arms 322 link pairs of rings 304 and 306, e.g., by connecting short bar arms 344 to 374 and short bar arms 340 to 370.

Stent pattern 300 has at least one second bar arm 378 connecting one of the pairs of rings to a ring of an adjacent pair of rings. Second bar arm 378 links a peak formed by large bar arms of a ring of a pair of rings to a valley formed by large bar arms of an adjacent ring of an adjacent pair of rings. For example, second bar arm 378 links rings 304 with 306A by connecting peak 320 with valley 350.

In some embodiments of stent 300, first bar arms 322 can be wider than second bar arms 378. Narrower second bar arms 378 can promote flexibility of stent 300. Wider first bar arms 322 can promote longitudinal stability of stent 300.

Substantial deformation may also occur in localized portions of the pattern of stent 300 in FIGS. 8 and 9 resulting in polymer chain alignment and possibly strain induced crystallization that increases the strength and modulus of these portions. When a stent having a pattern such as those depicted in FIGS. 8 and 9 is expanded, the bow-tie shaped cells tend to become narrower along the longitudinal axis and longer along the cylindrical axis of the stent.

As depicted in FIGS. 8 and 9, the short bar arms are shorter than longer bar arms. As discussed above, the short bar arms tend to plastically deform prior to the long bar arms. As stent 300 is expanded, short bar arms may tend to circumferentially align and become plastically deformed along their length. Therefore, the short bar arms may become substantially locked and rigid and act to provide resistance against recoil and inward radial forces. Long bar arms may tend to have less circumferential alignment. As a result, the deformation of the longer bar arms may be completely or substantially elastic. Thus, the longer bar arms may be relatively elastic and provide flexibility to the stent.

Also, the width of any of the bar arms of the cylindrical rings may also be varied to control the amount of deformation in the bar arms. As indicated above, the thinner the bar arm, the more readily it deforms under an applied stress.

Radial expansion of the stent pattern shown in FIGS. 8 and 9 cause the bow-tie-shaped cells to become narrower along the longitudinal axis as the stent expands. Substantial local deformation tends to occur at peaks and valleys due to a change in angle between bar arms, e.g. short bar arm 340 and long bar arm 332 and short bar arm 344 and long bar arm 336. As indicated above, plastic deformation occurs along the length of the short bar arms which tends to increase the radial strength of the stent and reduces recoil. Additionally, strain-induced crystallization can reduce long term creep in the stent.

In a similar manner, crimping of the stent pattern in FIGS. 8 and 9 causes the bow-tie-shaped regions to become wider along the longitudinal axis and longer along the circumferential direction. Substantial deformation also occurs at and proximate to the peaks and valleys.

The stent patterns disclosed herein are not limited in application to stents. The pattern may also be applied to other implantable medical devices including, but not limited to, self-expandable stents, balloon-expandable stents, stent-grafts, and vascular grafts.

Stent patterns for polymeric stents may be formed from a polymeric tube by laser cutting the pattern of struts in the tube. The stent may also be formed by laser cutting a polymeric sheet, rolling the pattern into the shape of the cylindrical stent, and providing a longitudinal weld to form the stent. Other methods of forming stents are well known and include chemically etching a polymeric sheet and rolling and then welding it to form the stent.

Polymer tubes used for fabricating stents may be formed by various methods. These include, but are not limited to, extrusion and injection molding. A tube used for fabricating a stent may be cylindrical or substantially cylindrical in shape. Conventionally extruded tubes tend to possess no or substantially no radial orientation or, equivalently, polymer chain alignment in the circumferential direction. In some embodiments, the diameter of the polymer tube prior to fabrication of an implantable medical device may be between about 0.2 mm and about 5.0 mm, or more narrowly between about 1 mm and about 3 mm.

Representative examples of polymers that may be used to fabricate embodiments of implantable medical devices disclosed herein include, but are not limited to, poly(N-acetylglucosamine) (Chitin), Chitosan, poly(3-hydroxyvalerate), poly(lactide-co-glycolide), poly(3-hydroxybutyrate), poly (4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating embodiments of implantable medical devices disclosed herein include ethylene vinyl alcohol copolymer (commonly known by the generic name EVOH or by the trade name EVAL), poly(butyl methacrylate), poly(vinylidene fluoride-co-hexafluoropropene) (e.g., SOLEF 21508, available from Solvay Solexis PVDF, Thorofare, NJ), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and polyethylene glycol.

EXAMPLES

An embodiment of the present invention is illustrated by the following set forth example. All parameters and data are not to be construed to unduly limit the scope of the embodiments of the invention.

FIG. 9 depicts an embodiment of the dimensions of stent 100 of FIG. 5. Measurements are given in inches with centimeters in brackets. The width of the bar arms of the hour-glass shaped cells is 0.008 in and the width of the linking bar arms is 0.006 in. The circumferential width across two diamond-shaped elements is 0.284 in and the longitudinal width across three diamond-shaped elements is 0.346 in. The radius of curvature of curved elements is as shown.

Figure 10:
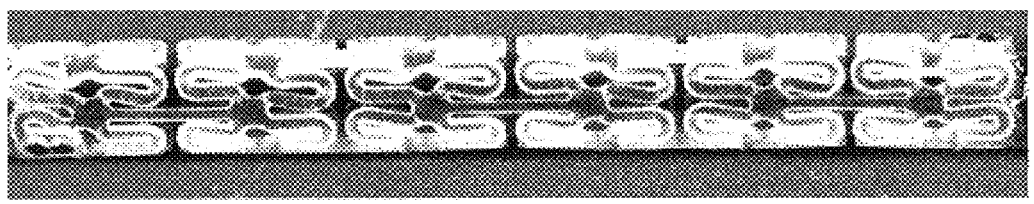
FIG. 10 depicts optical micrographs of a stent with a stent pattern shown in FIGS. 5 in a crimped condition.
Figure 11:
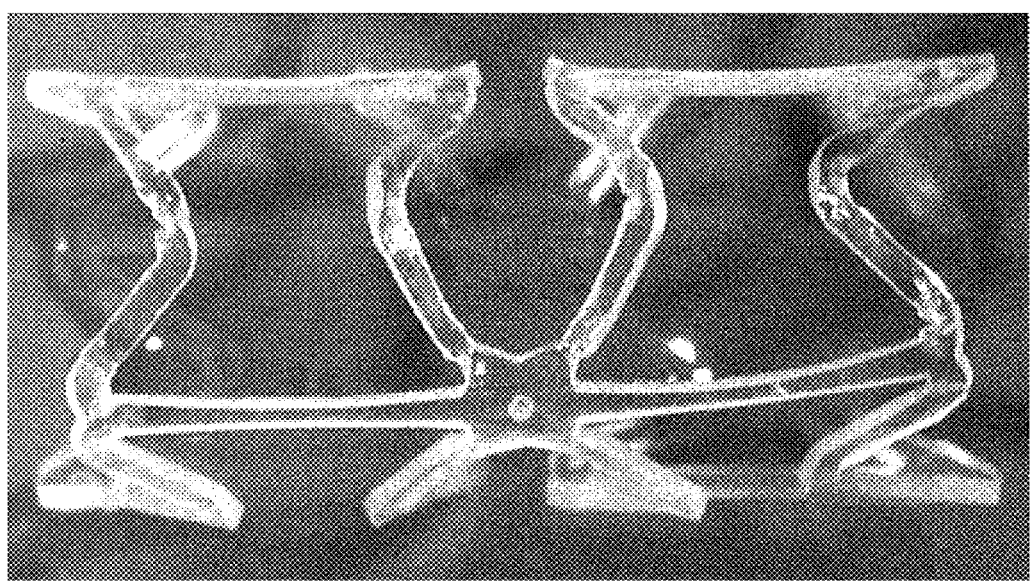
FIGS. 11-12 depict optical micrographs of a stent with a stent pattern shown in FIG. 5 in an expanded condition.
Figure 12:
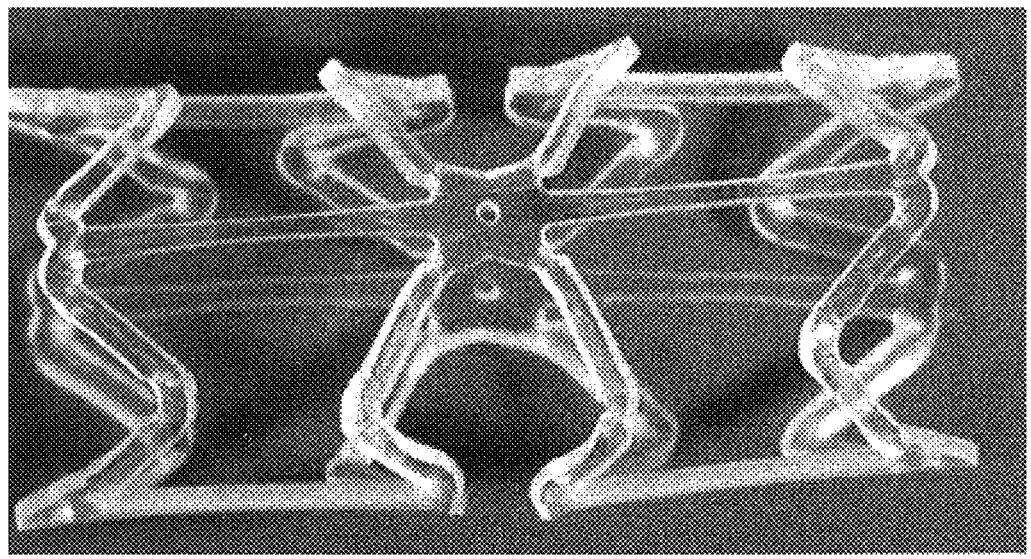

FIGS. 10-12 depict optical micrographs of an example of a stent with a stent pattern shown in FIGS. 5 and 6. FIG. 10 depicts the stent in a crimped condition. FIGS. 11 and 12 depict the stent in an expanded condition.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A radially expandable intravascular stent for implanting in a bodily lumen, comprising:
    a plurality of pairs of radially expandable undulating cylindrical rings that are longitudinally aligned and are connected at a plurality of intersections to form a plurality of hour-glass shaped cells, each ring having a first delivery diameter and a second implanted diameter,
        wherein a first ring of the pair comprises two v-shaped undulations with peaks located circumferentially between two intersections, and wherein the v-shaped undulations comprise long bar arms connected at each intersection, a short bar arm connected to each long bar arm, and a linear or curved bar arm connecting the two short bar arms of each v-shaped undulation;
        wherein a second ring of the pair comprises two v-shaped undulations with valleys located circumferentially between two intersections, and wherein the v-shaped undulation comprises a long bar arm connected at the intersection, a short bar arm connected to each long bar arm, and a linear or curved bar arm connecting the two short bar arms of each v-shaped undulation;
    a plurality of links comprising linear bar arms connecting adjacent rings, wherein at least one link joins an intersection of the plurality of intersections of a pair of one ring with a linear or curved bar arm of an adjacent ring.

2. The stent of claim 1, wherein at least two links intersect at one intersection such that the intersection comprises an intersection of two links and four long bar arms.

3. The stent of claim 1, wherein the short bar arms are shorter in length than the long bar arms, and each of the hour-glass shaped cells defines a continuous interior space that includes two quadrilateral-shaped regions, each region having a closed vertex and an open vertex, the closed vertex located where two long bar arms converge and meet each other, the open vertex located where two short bar arms converge but do not meet each other, the two regions meeting each other at the open vertices.

4. The stent of claim 3, wherein the hour-glass shaped cells of the first pair of rings are offset from the hour-glass shaped cells of a second pair of rings immediately adjacent the first pair of rings so that the closed vertices of the first pair of rings are longitudinally aligned with the open vertices of the second pair of rings.

5. The stent of claim 1, wherein a degree of circumferential alignment of a majority of the short bar arms is configured to increase when the stent is expanded to the second implanted diameter.

6. The stent of claim 1, wherein a majority of the short bar arms are configured to plastically deform when the stent is expanded the second implanted diameter.

7. A radially expandable intravascular stent for implanting in a bodily lumen, comprising:
    a plurality of radially expandable undulating cylindrical rings that are longitudinally aligned, each ring having:
    a first delivery diameter and a second implanted diameter;
    a plurality of interconnected cells, each cell formed by two opposing M-shaped elements aligned circumferentially and connected at each end of the elements to form an hour-glass shape, each M-shaped element comprising a long linear bar arm at each end of the M-shaped element, a short linear bar arm connected to each long linear bar arm, and a linear or curved bar arm connecting the short bar arms; and
    a plurality of links connecting adjacent cylindrical rings, wherein at least one link connects a connection point of two opposing M-shaped elements on one ring with a linear or curved bar arm of an adjacent ring.

8. The stent of claim 7, wherein the short bar arms are shorter in length than the long bar arms, and each of the hour-glass shaped cells define a continuous interior space that includes two quadrilateral-shaped regions, each region having a closed vertex and an open vertex, the closed vertex located where two long bar arms converge and meet each other, the open vertex located where two short bar arms converge but do not meet each other, the two regions meeting each other at the open vertices.

9. A radially expandable intravascular stent for implanting in a bodily lumen, comprising:
    a plurality of pairs of radially expandable undulating cylindrical rings that are longitudinally aligned, a first ring of the pair comprising adjacent pairs of first v-shaped sections with peaks formed by a long linear bar arm and a short linear bar arm of the first ring, the short linear bar arms of the first ring are connected by a linear or curved bar arm of the first ring, wherein the adjacent pairs of first v-shaped sections are separated by a second v-shaped section with a valley formed by the long linear bar arms, a second ring of the pairs of rings comprises adjacent pairs of third v-shaped sections with valleys formed by a long linear bar arm and a short linear bar arm of the second ring, the short linear bar arms of the second ring are connected by a linear or curved bar arm of the second ring, wherein the adjacent pairs of third v-shaped sections are separated by a fourth v-shaped section with a peak formed by the long linear bar arms of the second ring;

wherein the first ring and the second ring intersect at the valleys of the second v-shaped section of the first ring and the peaks of the fourth v-shaped section of the second ring to form an hourglass shape longitudinally between the pairs of rings and circumferentially between the intersections;

at least one link connecting the intersection of a pair of rings with a short linear or curved bar arm of an adjacent pair of rings.

10. The stent of claim 9, wherein at least two links intersect at one intersection such that the intersection comprises an intersection of two links and four long linear bar arms.

11. The stent of claim 9, wherein the short linear bar arms are shorter than the long linear bar arms, and each of the hour-glass shaped cells defines a continuous interior space that includes two quadrilateral-shaped regions, each region having a closed vertex and an open vertex, the closed vertex located where two long bar arms converge and meet each other, the open vertex located where two short bar arms converge but do not meet each other, the two regions meeting each other at the open vertices.

12. The stent of claim 9, wherein a degree of circumferential alignment of a majority of the short linear bar arms is configured to increase when the stent is expanded to the second delivery diameter.

13. The stent of claim 9, wherein a majority of the short linear bar arms are configured to plastically deform when the stent is expanded to the second delivery diameter.

14. A radially expandable intravascular stent for implanting in a bodily lumen, comprising:
a plurality of radially expandable undulating cylindrical rings that are longitudinally aligned, each ring having:
a first delivery diameter and a second implanted diameter;
a plurality of interconnected cells, each cell comprising:
two adjacent parallelogram-shaped regions, each region open at one end opposite a vertex such that the open ends are opposing, the cells being connected circumferentially at an intersection at the vertices opposite the open ends, each region comprising:
two long bar arms in a v-configuration connected at an adjacent cell at a vertex of the v-configuration, a longitudinal axis of the stent being perpendicular to a line through the vertices of the v-configurations of the two parallelogram-shaped regions;
two short bar arms, each of the short bar arms being connected at one end to the long bar arms;
two curved or linear bar arms connecting the opposing regions, each connecting ends of the short bar arms in the different regions; and
a plurality of links connecting adjacent cylindrical rings, wherein at least one link connects an intersection of circumferentially adjacent cells on one ring with a linear or curved bar arm of a longitudinally adjacent ring.

15. A radially expandable intravascular stent for implanting in a bodily lumen, comprising:
a plurality of pairs of radially expandable undulating cylindrical rings that are longitudinally aligned and are connected at a plurality of intersections on each pair by a plurality of first bar arms aligned parallel or substantially parallel to a longitudinal axis of the stent, each ring having a first delivery diameter and a second implanted diameter;
wherein a first ring of each pair comprises a peak between two valleys located circumferentially between two intersections of the first bar arms with the first ring, the peak formed by two long bar arms and each of the valleys formed by one of the long bar arms and a short bar arm,
wherein a second ring of each pair comprises a valley between two peaks located circumferentially between two intersections of the first bar arms with the second ring, the valley formed by two long bar arms and the peaks formed by one of the long bar arms and a short bar arm,
wherein the longitudinal distances from the two valleys of the first ring to the two peaks of the second ring are greater than the longitudinal distance from the peak of the first ring and the valley of the second ring,
wherein the first bar arms connect short bar arms of the first ring of the pairs to short bar arms of the second ring of the pairs at the intersections; and
at least one second bar arm connecting a peak of a first ring of a pair to a valley of a second ring of an adjacent pair of rings.

16. The stent of claim 15, wherein the short bar arms are shorter than the long bar arms.

17. The stent of claim 15, wherein at least one first bar arm is wider than at least one second bar arm.

18. The stent of claim 15, wherein a majority of the short bar arms are configured to plastically deform along their length when the stent is expanded to the second delivery diameter.

19. The stent of claim 15, wherein the at least one second bar arm is aligned parallel or substantially parallel to the longitudinal axis of the stent.

20. The stent of claim 15, wherein the at least one second bar arm is shorter than the first bar arms.

21. The stent of claim 15, wherein the first and second bar arms are parallel or substantially parallel to each other, and the first bar arms are not longitudinally aligned with the second bar arms so that the first bar arms are offset from the second bar arms.

22. A radially expandable intravascular stent for implanting in a bodily lumen, comprising:
a plurality of pairs of radially expandable undulating cylindrical rings that are longitudinally aligned, wherein a first ring of a pair from among the plurality of pairs comprises peaks formed by long linear bar arms alternating with peaks formed by short linear bar arms and valleys in between the peaks formed by short and long linear bar arms and a second ring of the pair comprises valleys formed by long linear bar arms alternating with valleys formed by short linear bar arms and peaks in between the valleys formed by short and long linear bar arms, wherein one of the peaks formed by the short bar arms of the first ring is connected to one of the valleys formed by the short bar arms of the second ring by a longitudinally aligned first bar arm; and
a plurality of longitudinally aligned second bar arms connecting the peaks formed by the long bar arms of the first ring of the pair to valleys formed by long bar arms of a second ring of an adjacent pair of rings.

23. The stent of claim 22, wherein the short bar arms are shorter than the long bar arms.

24. The stent of claim 22, wherein at least one first bar arm is wider than at least one second bar arm.

25. The stent of claim 22, wherein a majority of the short bar arms are configured to plastically deform along their length when the stent is expanded to the second delivery diameter.

26. The stent of claim 22, wherein the longitudinal distances from peaks formed by the long bar arms of the first ring of the pair to the valleys formed by the long bar arms of the second ring of the pair is less than the distances from the valleys of the first ring of the pair to the peaks of the second ring of the pair.

27. The stent of claim 22, wherein the second bar arms are shorter than the long bar arm.

28. The stent of claim 22, wherein the first and second bar arms are parallel or substantially parallel to a longitudinal axis of the stent, and the first bar arms are not longitudinally aligned with the second bar arms so that the first bar arms are offset from the second bar arms.

29. A radially expandable intravascular stent for implanting in a bodily lumen, comprising:

a plurality of pairs of undulating rings capable of expanding in circumference, the pairs of rings arranged adjacent to each other and connected to each other by linear links parallel or substantially parallel to a longitudinal axis of the stent, each of the pair of rings having a circumference that includes a series of cells connected to each other at intersections, each of the cells defining a continuous interior space that includes two interior regions, each of the interior regions defined by a series of at least four linear members and vertices between the linear members, the vertices including a closed vertex and an open vertex, the closed vertex located where two of the members converge and meet each other at one of the intersections, the open vertex located where another two of the members converge but do not meet each other, the two interior regions meeting each other at the open vertices.

30. The stent of claim 29, wherein the two interior regions of each cell are symmetrical or substantially symmetrical to each other;

wherein the at least four linear members of each interior region includes short members and long members greater in length than the short members;

wherein the open vertex of each interior region is located where two of the short members converge but do not meet each other;

wherein the open vertices of a first pair of rings are longitudinally aligned with the closed vertices of a second pair of rings immediately adjacent the first pair of rings; and wherein the linear links have a first end and a second end, the first end located adjacent the open vertices of the first pair of rings, the second end located adjacent the closed vertices of the second pair of rings.

31. The stent of claim 29, wherein the two interior regions of each cell are symmetrical or substantially symmetrical to each other;

wherein the at least four linear members of each interior region includes short members and long members greater in length than the short members;

wherein the open vertex of each interior region is located where two of the long members converge but do not meet each other;

wherein the open vertices of the first pair of rings are longitudinally aligned with the open vertices of a second pair of rings immediately adjacent the first pair of rings; and wherein the linear links have a first end and a second end, the first end located adjacent the open vertices of the first pair of rings, the second end located adjacent the open vertices of the second pair of rings.

* * * * *